United States Patent
Koseoglu et al.

(10) Patent No.: US 10,571,452 B2
(45) Date of Patent: *Feb. 25, 2020

(54) CHARACTERIZATION OF CRUDE OIL BY HIGH PRESSURE LIQUID CHROMATOGRAPHY

(71) Applicant: Saudi Arabian Oil Company, Dhahran (SA)

(72) Inventors: Omer Refa Koseoglu, Dhahran (SA); Adnan Al-Hajji, Dhahran (SA); Saroj Kumar Panda, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 251 days.

This patent is subject to a terminal disclaimer.

(21) Appl. No.: 15/639,574

(22) Filed: Jun. 30, 2017

(65) Prior Publication Data

US 2017/0363603 A1 Dec. 21, 2017

Related U.S. Application Data

(63) Continuation-in-part of application No. 13/468,105, filed on May 10, 2012, now abandoned, and a
(Continued)

(51) Int. Cl.
*G01N 33/28* (2006.01)
*G01N 30/86* (2006.01)
(Continued)

(52) U.S. Cl.
CPC ..... *G01N 33/2823* (2013.01); *G01N 30/8675* (2013.01); *G01N 30/88* (2013.01);
(Continued)

(58) Field of Classification Search
CPC .............. G01N 30/8675; G01N 30/88; G01N 2030/027; G01N 2030/8854; G01N 33/2811; G01N 33/2823; G01N 33/2829
See application file for complete search history.

(56) References Cited

U.S. PATENT DOCUMENTS 3,617,501 A 11/1971 Eng
3,896,312 A 7/1975 Brown
(Continued)

FOREIGN PATENT DOCUMENTS

CA 2781273 A1 12/2013
EP 0305090 A2 8/1988
(Continued)

OTHER PUBLICATIONS

Adhvaryu, A. et al., Quantitative NMR Spectroscopy for the Prediction of Base Oil Properties, Tribology Transactions, vol. 43, No. 2, 2000, pp. 245-250.
(Continued)

*Primary Examiner* — Natalie Huls
(74) *Attorney, Agent, or Firm* — Abelman, Frayne & Schwab

(57) ABSTRACT

A system and a method are provided for calculating one or more indicative properties, e.g., one or more of the cetane number, octane number, pour point, cloud point and aniline point of oil fractions, from the density and high pressure liquid chromatography (HPLC) data of a sample of the crude oil.

20 Claims, 4 Drawing Sheets

Related U.S. Application Data continuation-in-part of application No. PCT/US2016/012151, filed on Jan. 5, 2016.

(60) Provisional application No. 61/501,962, filed on Jun. 28, 2011, provisional application No. 62/099,763, filed on Jan. 5, 2015.

(51) Int. Cl.
*G01N 30/88* (2006.01)
*G01N 30/02* (2006.01)

(52) U.S. Cl.
CPC ..... *G01N 33/2811* (2013.01); *G01N 33/2829* (2013.01); *G01N 2030/027* (2013.01); *G01N 2030/8854* (2013.01)

(56) References Cited

U.S. PATENT DOCUMENTS

| | | | |
|---|---|---|---|
| 4,251,870 A | 2/1981 | Jaffe | |
| 4,826,603 A * | 5/1989 | Hayes, Jr. | G01N 30/461 210/635 |
| 4,897,177 A | 1/1990 | Nadler | |
| 4,971,915 A | 11/1990 | Schwartz et al. | |
| 4,988,446 A * | 1/1991 | Haberman | C10G 11/187 210/198.2 |
| 5,121,337 A | 6/1992 | Brown | |
| 5,223,714 A | 6/1993 | Maggard | |
| 5,266,800 A | 11/1993 | Mullins | |
| 5,304,807 A | 4/1994 | Lin | |
| 5,424,959 A | 6/1995 | Reyes | |
| 5,452,232 A | 9/1995 | Espinosa et al. | |
| 5,475,612 A | 12/1995 | Espinosa | |
| 5,490,085 A | 2/1996 | Lambert et al. | |
| 5,572,030 A | 11/1996 | Ranson et al. | |
| 5,600,134 A | 2/1997 | Ashe et al. | |
| 5,602,755 A | 2/1997 | Ashe et al. | |
| 5,656,810 A | 8/1997 | Alfano et al. | |
| 5,699,269 A | 12/1997 | Ashe et al. | |
| 5,699,270 A | 12/1997 | Ashe et al. | |
| 6,070,128 A | 5/2000 | Descales | |
| 6,258,987 B1 | 7/2001 | Schmidt et al. | |
| 6,275,775 B1 | 8/2001 | Baco | |
| 6,490,029 B1 | 12/2002 | Cho | |
| 6,602,403 B1 | 8/2003 | Steffens et al. | |
| 6,611,735 B1 | 8/2003 | Henly | |
| 6,633,043 B2 | 10/2003 | Hegazi | |
| 6,662,116 B2 | 12/2003 | Brown | |
| 6,711,532 B1 | 3/2004 | Spieksma | |
| 6,841,779 B1 | 1/2005 | Roehner et al. | |
| 6,893,874 B2 | 5/2005 | Stark | |
| 7,126,332 B2 | 10/2006 | Blanz | |
| 7,173,239 B2 | 2/2007 | DiFoggio | |
| 7,560,711 B2 | 7/2009 | Hegazi | |
| 7,598,487 B2 * | 10/2009 | Qian | G01N 30/7206 250/282 |
| 8,714,246 B2 | 5/2014 | Pop et al. | |
| 8,887,557 B2 * | 11/2014 | Chawla | B01D 15/1871 210/660 |
| 8,930,149 B1 | 1/2015 | Koseoglu et al. | |
| 9,285,307 B2 | 3/2016 | Koseoglu et al. | |
| 9,423,391 B2 | 8/2016 | Koseoglu et al. | |
| 9,429,556 B2 | 8/2016 | Koseoglu et al. | |
| 9,778,240 B2 | 10/2017 | Koseoglu et al. | |
| 9,816,919 B2 | 11/2017 | Koseoglu et al. | |
| 2002/0052769 A1 | 5/2002 | Navani et al. | |
| 2003/0141459 A1 | 7/2003 | Hegazi et al. | |
| 2003/0195708 A1 * | 10/2003 | Brown | G01N 21/35 702/22 |
| 2005/0109934 A1 | 5/2005 | David | |
| 2005/0173298 A1 | 8/2005 | Wellington | |
| 2006/0043004 A1 | 3/2006 | Rose | |
| 2006/0047444 A1 | 3/2006 | Brown | |
| 2006/0142955 A1 | 6/2006 | Jones | |
| 2007/0050154 A1 | 3/2007 | Albahri | |
| 2007/0231912 A1 | 10/2007 | Reischman et al. | |
| 2007/0295640 A1 | 12/2007 | Tan et al. | |
| 2008/0037006 A1 | 2/2008 | Canas Triana | |
| 2008/0040051 A1 | 2/2008 | Franklin et al. | |
| 2008/0206887 A1 | 8/2008 | Chen | |
| 2008/0248967 A1 | 10/2008 | Butler et al. | |
| 2008/0253426 A1 | 10/2008 | Voelkening | |
| 2008/0260584 A1 | 10/2008 | Gudde et al. | |
| 2009/0011517 A1 | 1/2009 | Hodges | |
| 2009/0105966 A1 * | 4/2009 | Brown | G01N 33/2823 702/30 |
| 2009/0180949 A1 | 7/2009 | Cui | |
| 2009/0279072 A1 | 11/2009 | Arakawa | |
| 2009/0290144 A1 | 11/2009 | Hegazi | |
| 2009/0316139 A1 | 12/2009 | Shrestha | |
| 2010/0049681 A1 * | 2/2010 | Pradhan | G01N 24/08 706/21 |
| 2010/0113311 A1 | 5/2010 | Eccleston et al. | |
| 2010/0204925 A1 | 8/2010 | Albahri | |
| 2010/0211329 A1 | 8/2010 | Farquharson et al. | |
| 2010/0218585 A1 * | 9/2010 | Chawla | G01N 30/462 73/1.02 |
| 2011/0152136 A1 | 6/2011 | Hughes et al. | |
| 2011/0308996 A1 | 12/2011 | Choudhary | |
| 2012/0171151 A1 | 7/2012 | Thomassian | |
| 2014/0075827 A1 | 3/2014 | Gonzalez et al. | |
| 2014/0156241 A1 | 6/2014 | Kumar et al. | |
| 2015/0106027 A1 | 4/2015 | Koseoglu et al. | |
| 2015/0106028 A1 | 4/2015 | Koseoglu et al. | |
| 2015/0106029 A1 | 4/2015 | Koseoglu et al. | |
| 2015/0106031 A1 | 4/2015 | Koseoglu et al. | |
| 2015/0112610 A1 | 4/2015 | Koseoglu | |
| 2015/0112611 A1 | 4/2015 | Koseoglu | |
| 2016/0011102 A1 | 1/2016 | Koseoglu et al. | |
| 2016/0187253 A1 | 6/2016 | Koseoglu et al. | |
| 2016/0195481 A1 | 7/2016 | Koseoglu | |
| 2016/0195507 A1 | 7/2016 | Koseoglu | |
| 2016/0195508 A1 | 7/2016 | Al-Hajji | |
| 2016/0377589 A1 | 12/2016 | Koseoglu | |
| 2017/0003217 A1 | 1/2017 | Koseoglu | |
| 2017/0363540 A1 | 12/2017 | Koseoglu | |
| 2017/0363591 A1 | 12/2017 | Koseoglu | |
| 2017/0363602 A1 | 12/2017 | Koseoglu | |
| 2017/0363603 A1 | 12/2017 | Koseoglu | |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0859236 A1 | 8/1998 |
| EP | 0984277 A1 | 3/2000 |
| SU | 817486 A1 | 3/1981 |
| SU | 1523972 A1 | 11/1989 |
| WO | 03/048759 A1 | 6/2003 |
| WO | 2004033513 A2 | 4/2004 |
| WO | 2006030218 A1 | 3/2006 |
| WO | 2009082418 A2 | 7/2009 |
| WO | 2013102916 A1 | 7/2013 |

OTHER PUBLICATIONS

Albahri, T. et al, Octane Number and Aniline Point of Petroleum Fuels, 2002, Fuel Chemistry Division, vol. 47(2), pp. 710-711.

Ali, M., Resolution and Quantification of Ring Type Aromatics by HPLC Method using N-Hexane Elution, 2003, King Fahd University of Petroleum and Minerals, pp. 1-9.

ASTM D2887-01, Standard Test Method for Boiling Range Distribution of Petroleum Fractions by Gas Chromatography, Annual Book of ASTM Standards, vol. 14, No. 02, pp. 204-216.

Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).

(56) References Cited

OTHER PUBLICATIONS

Bowden, J. et al., Octane-Cetane Relationship, 1974, NTIS, p. 8.
Chemstations, Inc., Physical Properties User's Guide, 2004, Chemstations Inc., Ver. 5.4, pp. 18-22.
Cookson, D.J. et al., Investigation of the Chemical Basis of Diesel Fuel Properties, Energy & Fuels, vol. 2, No. 6, 1988, pp. 854-860.
Duvekot, C., Fast Analysis of Paraffins, iso-Paraffins, Olefins, iso-Olefins, Naphthenes and Aromatics in Hydrocarbon Streams, Varian, Inc., 2008, pp. 1-4.
Evokimov, I, et al, Potential of UV-Visible Absorption Spectroscopy for characterizing Crude Petroleum Oils, Oil an Gas Business, 2007, 21 pages.
Falla, F, et al., Characterization of crude petroleum by NIR, Journal of Petroleum Science and Engineering, vol. 51, 2006, pp. 127-137.
Fernandez-Lima, F. et al., Petroleum Crude Oil Characterization by IMS-MS and FTICR MS, 2009, American Chemical Society, Ed. 81, pp. 9941-9945.
Grizzle, P. et al., Automated Liquid Chromatographic Compound Class Group-Type Separation of Crude Oils and Bitumens Using Chemically Bonded Aminolilane, 1986, Publisher Anal. Chem., vol. 58, pp. 2389-2390.
Hasan, M.U. et al., Structural characterization of Saudi Arabian heavy crude oil by n.m.r. spectroscopy, Fuel, vol. 62, 1983, pp. 518-523.
Hidajat, K, et al., Quality characterisation of crude oils by partial least square calibration of NIR spectral profiles, Near Infrared Spectrosc, vol. 8, pp. 53-59, 2000.
Jokuty, P. et al., Hydrocarbon Groups and Their Relationships to Oil Properties and Behavior, 1995, Published by Whiticar Scientific, p. 11.
Khanmohammadi, M, et al., Characterization of petroleum-based products by infrared spectroscopyu and chemometrics, Trac Trends in Analytical Chem, vol. 35, 2012.
Kok, M, et al., High pressure TGA analysis of crude oils, Thermochimica Acta., vol. 287, No. 1, 1996, pp. 91-99.
Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.

Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.
Pande, S., et al., Cetana Number Predictions of a Trial Index Based on Compositional Analysis, American Chemical Society, 1989, pp. 308-312.
Patra, D, et al, Determination of Synchronous Fluorescence Scan Parameters for Certain Petroleum Products, Journal of Scientific & Industrial Research, Apr. 1, 2000, pp. 300-305.
Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).
Pereira,Thieres M. C., An evaluation of the aromaticity of asphaltenes using atmospheric pressure photoionization Fourier transform ion cyclotron resonance mass spectrometry—APP (±) FT-ICR MS, Fuel, 2014, vol. 118, 2014, pp. 348-357.
Rodgers, R. et al., Advanced Characterization of Petroleum Crude and Products by High Field Fourier Transform Ion Cyclotron Resonance Mass Spectrometry, 2002, Fuel Chemistry Division, Ed. 47(2), pp. 636-637.
Shea, T.M., Modeling Base Oil Properties using NMR Spectroscopy and Neural Networks, Tribology Transactions, vol. 46, No. 3, 2003, pp. 296-302.
Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.
Speight, Handbook of Petroleum Product Analysis, 2002.
Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.
University of Oldenburg, Institute of Physics, Catalogue of Optical Spectra of Oils, Jan. 2005, retrieved from http://las.physik.uni-oldenburg.de/data/spectra/indez.htm, 6 pages.
Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.
PCT/US2016/012151, International Search Report and Written Opinion dated May 17, 2016, 18 pages.

* cited by examiner

CHARACTERIZATION OF CRUDE OIL BY HIGH PRESSURE LIQUID CHROMATOGRAPHY

RELATED APPLICATIONS

This application is a Continuation-in-Part of
U.S. patent application Ser. No. 13/468,105 filed May 10, 2012, claiming priority from U.S. Provisional Patent Application No. 61/501,962 filed Jun. 28, 2011; and PCT/US2016/012151 filed Jan. 5, 2016, claiming priority from U.S. Provisional Patent Application No. 62/099,763 filed Jan. 5, 2015;
the disclosures of which are hereby incorporated by reference in their entireties.

FIELD OF THE INVENTION

This invention relates to a method and process for the evaluation of samples of crude oil and its fractions by high pressure liquid chromatography (HPLC).

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, °C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy Gas Oil | 315-370 |
| Light Vacuum Gas Oil | 370-430 |
| Mid Vacuum Gas Oil | 430-480 |
| Heavy Vacuum Gas oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |

TABLE 2-continued

| Property | Unit | Property Type | Fraction |
| --- | --- | --- | --- |
| Smoke Point, mm | mm | Indicative | Fraction boiling between 150-250 |
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°–180° C.), kerosene (180°–240° C.), gas oil (240°–370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°–520° C., and vacuum residue, comprising hydrocarbons boiling above 520° C. The crude assay data help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description are given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two separate phases are again formed is recorded as the aniline point or mixed aniline point.

To determine these properties of gas oil or naphtha fractions conventionally, these fractions have to be distilled from the crude oil and then measured/identified using various analytical methods that are laborious, costly and time-consuming.

High pressure liquid chromatography or high-performance liquid chromatography (HPLC) is a technique that can separate a mixture of compounds into individual analytes or into a group of analytes, depending on the complexity of the sample. HPLC serves various analytical applications including identification, quantification and/or purification of an individual component or a group of components having similar properties.

Any new rapid, direct method to help better understand the crude oil composition and properties from the analysis of whole crude oil will save producers, marketers, refiners and/or other crude oil users substantial expense, effort and time. Therefore, a need exists for an improved system and method for determining the properties of crude oil fractions from different sources and classifying the crude oil fractions based on their boiling point characteristics and/or properties.

SUMMARY OF THE INVENTION

Systems and methods for determining the indicative properties of a hydrocarbon sample are provided. In accordance with the invention, indicative properties (i.e., cetane number, pour point, cloud point and aniline point of gas oil fraction and octane number of gasoline fraction in crude oils) are predicted by density and HPLC measurement of crude oils. The correlations also provide information about the gas oil properties without fractionation/distillation (crude oil assays) and will help producers, refiners, and marketers to benchmark the oil quality and, as a result, evaluate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings in which.

DETAILED DESCRIPTION OF INVENTION

A system and method is provided for determining one or more indicative properties of a hydrocarbon sample. Indicative properties (e.g., one or more of cetane number, pour point, cloud point and aniline point) of a gas oil fraction in crude oil samples are assigned as a function of density and HPLC measurement of crude oils.

HPLC is carried out on oil samples. HPLC operates in various modes, such as normal phase, reversed phase, ion exchange, gel permeation, and hydrophilic interaction, which are defined by the combination of stationary phases and mobile phases. In certain embodiments herein, normal phase chromatography is used; where the stationary phase is polar and the mobile phase is non-polar. HPLC typically utilizes different types of stationary phases for different applications, a pump that moves the mobile phase(s) and analytes through the column, and a detector to provide a characteristic retention time for the analytes. The detector may also provide additional information related to the analytes. Analyte retention time varies depending on the strength of its interactions with the stationary phase, the ratio/composition of solvent(s) used, and the flow rate of the mobile phase.

The correlations provide information about gas oil and/or naphtha indicative properties without fractionation/distillation (crude oil assays) and will help producers, refiners, and marketers to benchmark the oil quality and, as a result, evaluate the oils without performing the customary extensive and time-consuming crude oil assays. The currently used crude oil assay method is costly in terms of money and time. It costs about $50,000 US and takes two months to complete one assay. With the method and system herein, the crude oil can be classified as a function of HPLC data, and thus decisions can be made for purchasing and/or processing.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction. Samples can be obtained from various sources, including an oil well, stabilizer, extractor, or distillation tower.

Figure 2:
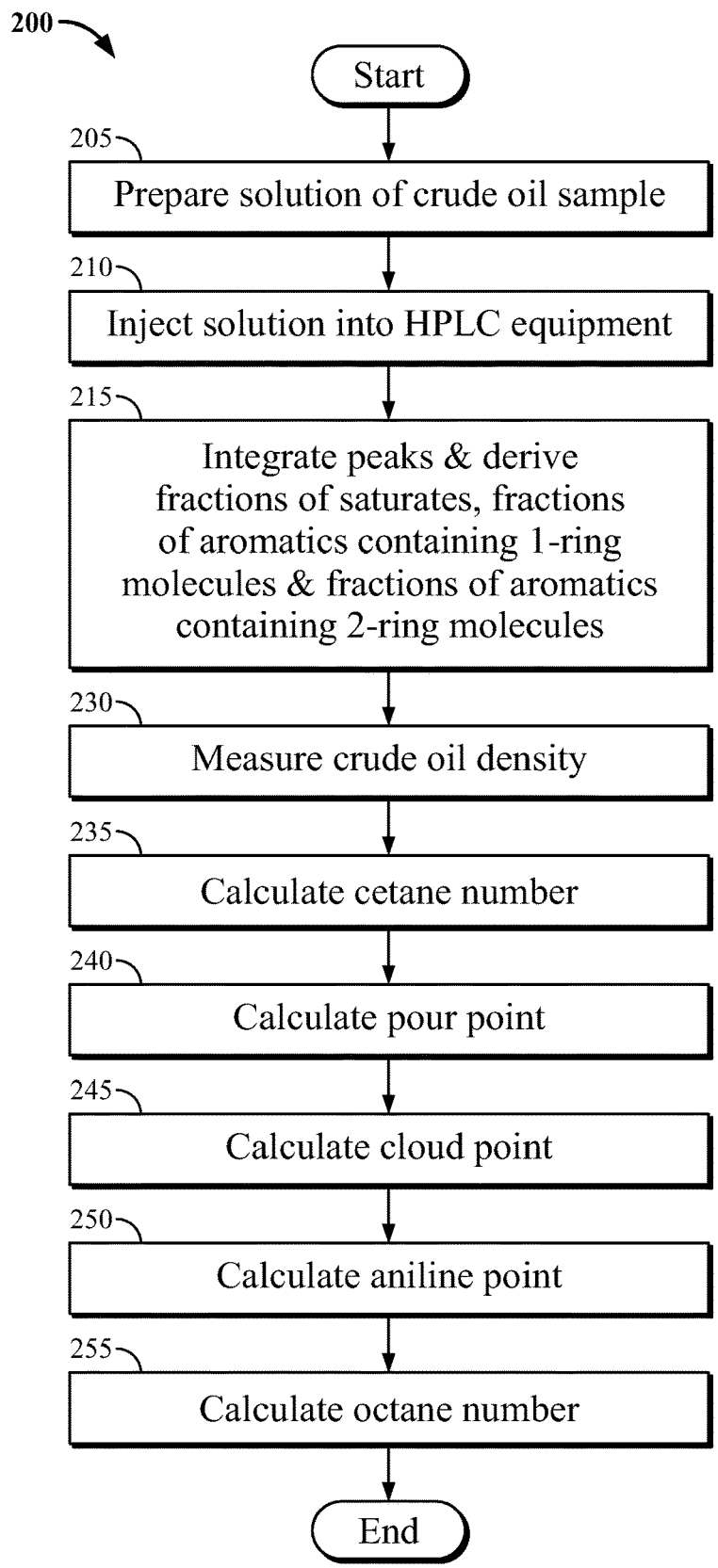
FIG. 2 is a block diagram of a method in which an embodiment herein is implemented.

In the system and method herein, a chromatogram is obtained by a suitable known or to be developed HPLC. FIG. 2 shows a process flowchart in a method 200 according to one embodiment herein. A solution of an oil sample is prepared, step 205. The prepared solution is injected into HPLC equipment, step 210. In step 215, the peaks are integrated to obtain a relevant percentage of each peak, e.g., saturates, aromatics containing 1-ring molecules, aromatics containing 2-ring molecules and aromatics containing 3 or more aromatic rings.

Figure 3:
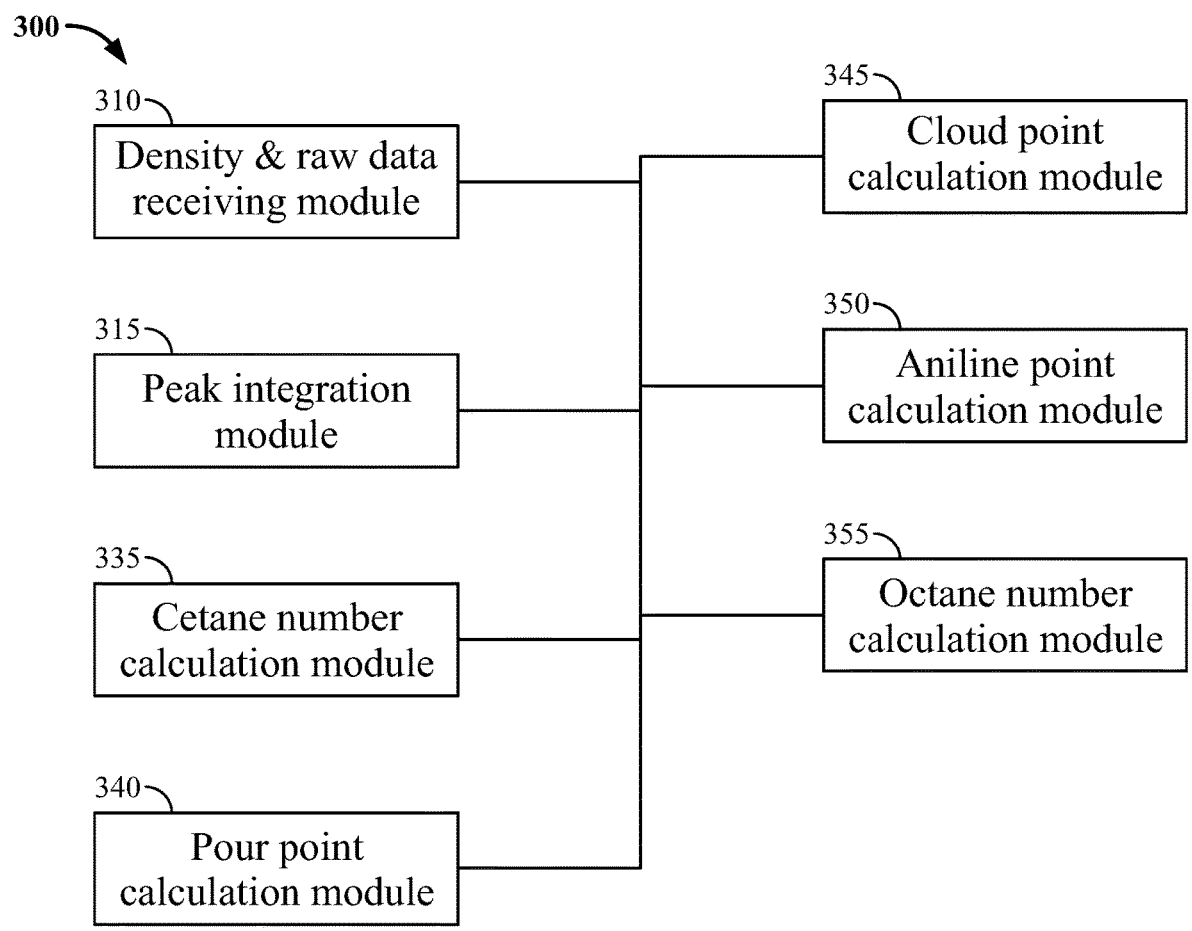
FIG. 3 is a schematic block diagram of modules of an embodiment herein.

FIG. 3 illustrates a schematic block diagram of modules in accordance with an embodiment of the present invention, system 300. Density and raw data receiving module 310 receives the density of a sample of crude oil and high pressure liquid chromatography (HPLC) data derived from the crude oil. Peak integrating module 315 integrates the peaks derived from the HPLC and calculates the fraction of saturates, fraction of aromatics containing 1-ring molecules and fraction of aromatics containing 2-ring molecules.

Cetane number calculation module 335 derives the cetane number for the gas oil fraction as a function of the density of the sample, the fraction of saturates, the fraction of aromatics containing 1-ring molecules, and the fraction of aromatics containing 2-ring molecules.

Pour point calculation module 340 derives the pour point for the gas oil fraction as a function of the density of the sample, the fraction of saturates, the fraction of aromatics containing 1-ring molecules, and the fraction of aromatics containing 2-ring molecules.

Cloud point calculation module 345 derives the cloud point for the gas oil fraction as a function of the density of the sample, the fraction of saturates, the fraction of aromatics containing 1-ring molecules, and the fraction of aromatics containing 2-ring molecules.

Aniline point calculation module 350 derives the aniline point for the gas oil fraction as a function of the density of the sample, the fraction of saturates, the fraction of aromatics containing 1-ring molecules, and the fraction of aromatics containing 2-ring molecules.

Octane number calculation module 355 derives the octane number for the gasoline fraction as a function of the density of the sample, the fraction of saturates, the fraction of aromatics containing 1-ring molecules, and the fraction of aromatics containing 2-ring molecules.

Figure 4:
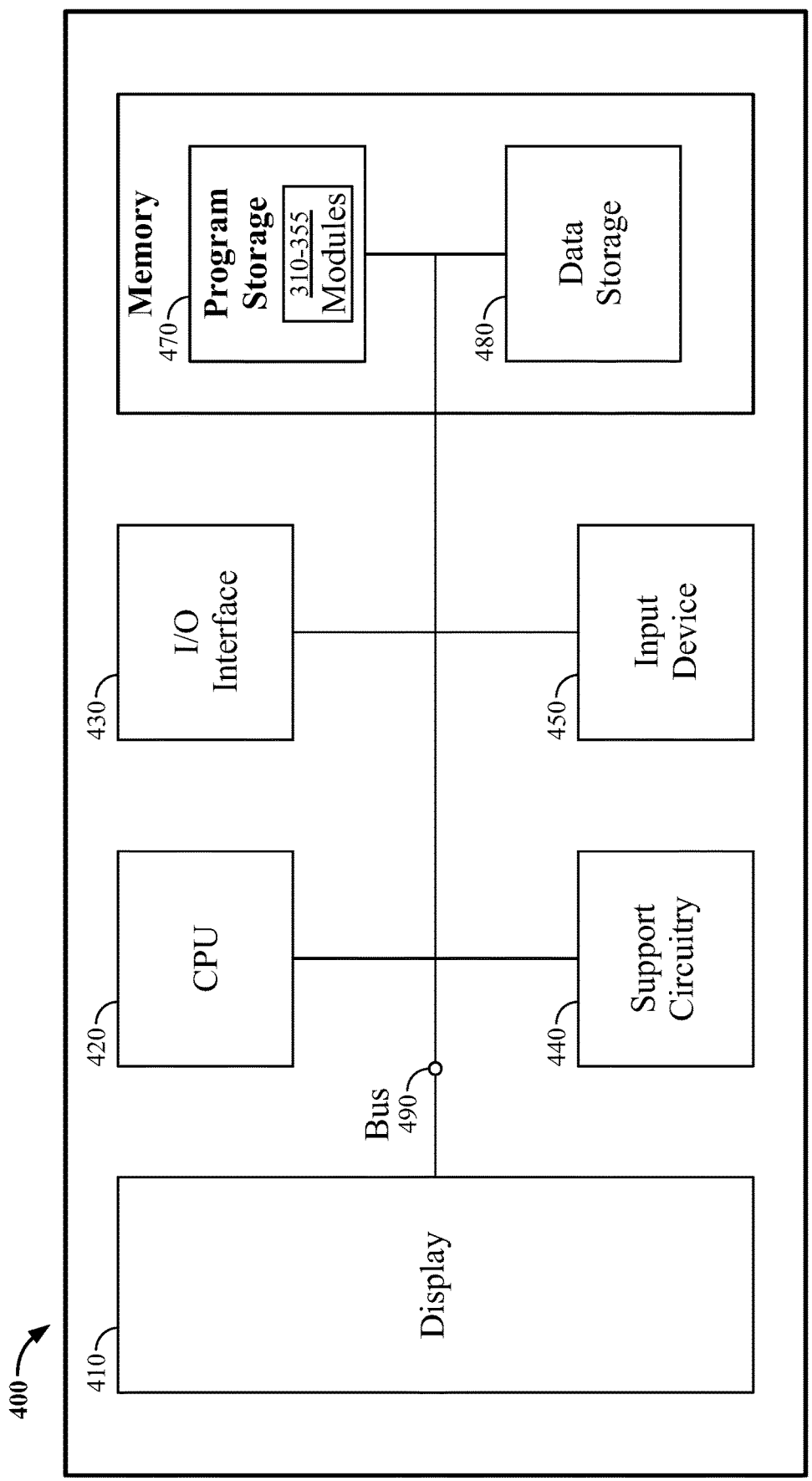
FIG. 4 is a block diagram of a computer system in which an embodiment herein is implemented.

FIG. 4 shows an exemplary block diagram of a computer system 400 in which the partial discharge classification system of the present invention can be implemented. Computer system 400 includes a processor 420, such as a central processing unit, an input/output interface 430 and support circuitry 440. In certain embodiments, where the computer system 400 requires a direct human interface, a display 410 and an input device 450 such as a keyboard, mouse or pointer are also provided. The display 410, input device 450, processor 420, and support circuitry 440 are shown connected to a bus 490 which also connects to a memory 460. Memory 460 includes program storage memory 470 and data storage memory 480. Note that while computer system 400 is depicted with direct human interface components display 410 and input device 450, programming of modules and exportation of data can alternatively be accomplished over the input/output interface 430, for instance, where the computer system 400 is connected to a network and the programming and display operations occur on another associated computer, or via a detachable input device as is known with respect to interfacing programmable logic controllers.

Program storage memory 470 and data storage memory 480 can each comprise volatile (RAM) and non-volatile (ROM) memory units and can also comprise hard disk and backup storage capacity, and both program storage memory 470 and data storage memory 480 can be embodied in a single memory device or separated in plural memory devices. Program storage memory 470 stores software program modules and associated data, and in particular stores a density and raw data receiving module 310, peak integrating module 315, cetane number calculation module 330, pour point calculation module 340, cloud point calculation module 345, aniline point calculation module 350, and octane number calculation module 355. Data storage memory 480 stores results and other data generated by the one or more modules of the present invention.

The calculated and assigned results in accordance with the systems and methods herein are displayed, audibly outputted, printed, and/or stored to memory for use as described herein.

It is to be appreciated that the computer system 400 can be any computer such as a personal computer, minicomputer, workstation, mainframe, a dedicated controller such as a programmable logic controller, or a combination thereof. While the computer system 400 is shown, for illustration purposes, as a single computer unit, the system can comprise a group of computers which can be scaled depending on the processing load and database size.

Computer system 400 preferably supports an operating system, for example stored in program storage memory 470 and executed by the processor 420 from volatile memory. According to the present system and method, the operating system contains instructions for interfacing the device 400 to the calculation module(s). According to an embodiment of the invention, the operating system contains instructions for interfacing computer system 400 to the Internet and/or to private networks.

Example

Crude oil samples were prepared and analyzed by HPLC according to the method 200 described below, and illustrated in FIG. 2.

In step 205, about 100 mg of crude oil sample is dissolved in 1 mL heptane. The solution is shaken thoroughly by a Vortex Mixer and allowed to stand for 10 minutes, after which it is filtered through a 0.45 μm Millipore filter in order to remove insoluble particles.

In step 210, the filtered sample is then directly injected into the HPLC equipment, consisting of a micro vacuum degasser, binary pump, column thermostat, auto-sampler and refractive index detector. The HPLC conditions maintained for this analysis are presented in the Table 3.

TABLE 3

| | |
|---|---|
| Flow rate: | 0.8 mL/min |
| Detector: | Refractive index detector, Optical unit temperature 30° C. |
| Injection volume: | 10 μL |
| Run time: | 40 minutes |
| Forward flush | 11.4 minute |
| Back flush | 11.4-30 minute |
| Mobile phase: | n-heptane |
| Column storage: | n-heptane |
| Injector needle wash: | n-heptane |
| Column: | LiChrospher $NH_2$ (250 × 4.6 mm) |
| Column temperature: | 25° C. |

Figure 1:
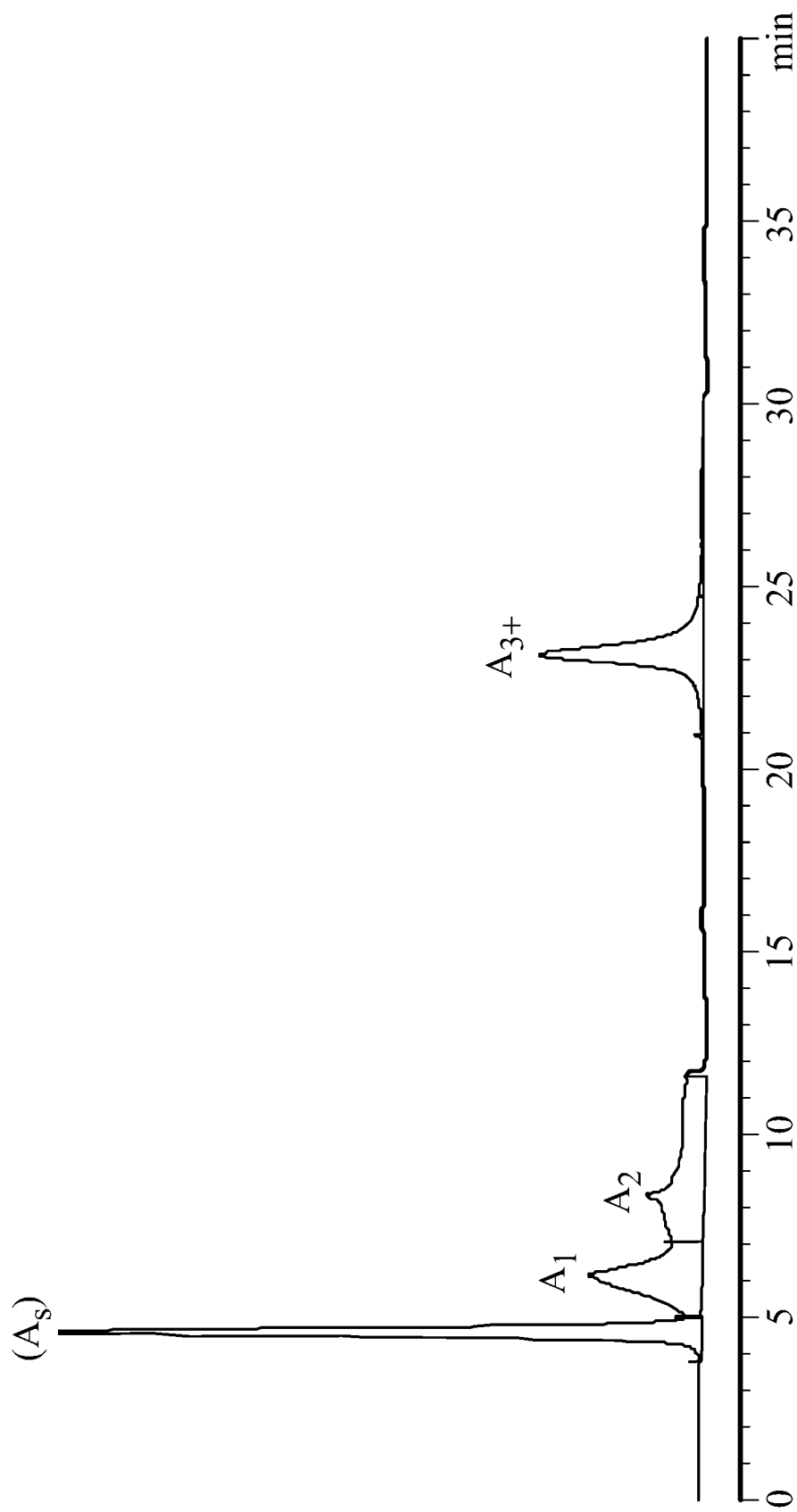
FIG. 1 is a graphic plot of typical HPLC data for a typical crude oil sample.

As the chromatogram of FIG. 1 shows, four peaks are obtained. The area under these peaks are: $A_s$, the peak area of saturates; $A_1$, the peak area of 1-aromatic rings; $A_2$, the peak area of 2-aromatic rings; and $A_{3+}$, the peak area of 3+-aromatic rings.

In step 215, the peaks are manually integrated using Agilent ChemStation software, though any similar software may be used. The relevant percentage of each peak is reported as:

$$\text{Fraction of saturates (SAT)} = A_s/(A_s+A_1+A_2+A_{3+}) \quad (1);$$

$$\text{Fraction of aromatics containing 1-ring molecules (AROM-1R)} = A_1/(A_s+A_1+A_2+A_{3+}) \quad (2);$$

$$\text{Fraction of aromatics containing 2-ring molecules (AROM-2R)} = A_2/(A_s+A_1+A_2+A_{3+}) \quad (3);$$

$$\text{Fraction of aromatics containing 3 or more aromatic rings} = A_{3+}/(A_s+A_1+A_2+A_{3+}) \quad (4).$$

The indicative properties (e.g., the cetane number, pour point, cloud point and aniline point of the gas oil fraction boiling in the range 180-370° C. and octane number for gasoline fraction boiling in the range 36-180° C.) of the crude oil can be predicted from the density of whole crude oil and the group type composition (saturates, 1-, 2-ring aromatics) of crude oil, as determined by HPLC. That is, $$\text{Indicative Property} = f(\text{density}_{crude\ oil}, \text{SAT}_{crude\ oil}, \text{AROM-1R}_{crude\ oil}, \text{AROM-2R}_{crude\ oil}) \quad (5);$$

Equations (6) through (9) show, respectively, the cetane number, pour point, cloud point and aniline point of gas oils boiling in the range 180-370° C., and equation (10) shows the octane number of gasoline boiling in the range 36-180° C. that can be predicted from the density (which is determined in step 230) and 1- and/or 2-ring aromatics composition of crude oils. Thus, in step 235, the cetane number is calculated as:

$$\text{Cetane Number (CET)} = K_{CET} + X1_{CET}*\text{DEN} + X2_{CET}*\text{SAT} + X3_{CET}*\text{AROM-1}R + X4_{CET}*\text{AROM-2}R \quad (6);$$

In step 240, the pour point is calculated as:

$$\text{Pour Point (PPT)} = K_{PPT} + X1_{PPT}*\text{DEN} + X2_{PPT}*\text{SAT} + X3_{PPT}*\text{AROM-1}R + X4_{PPT}*\text{AROM-2}R \quad (7)$$

In step 245, the cloud point is calculated as:

$$\text{Cloud Point (CPT)} = K_{CPT} + X1_{CPT}*\text{DEN} + X2_{CPT}*\text{SAT} + X3_{CPT}*\text{AROM-1}R + X4_{CPT}*\text{AROM-2}R \quad (8)$$

In step 250, the aniline point is calculated as:

$$\text{Aniline Point (AP)} = K_{AP} + X1_{AP}*\text{DEN} + X2_{AP}*\text{SAT} + X3_{AP}*\text{AROM-1}R + X4_{AP}*\text{AROM-2}R \quad (9)$$

In step 255, the octane number is calculated as:

$$\text{Octane Number (ON)} = K_{ON} + X1_{ON}*\text{DEN} + X2_{ON}*\text{SAT} + X3_{ON}*\text{AROM-1}R \quad (10)$$

where:
DEN = density of the crude oil sample;
SAT = Fraction of saturates by HPLC;
AROM-1R = Fraction of aromatics containing 1-ring molecules by HPLC;
AROM-2R = Fraction of aromatics containing 2-ring molecules by HPLC; and
$K_{CET}$, $X1_{CET}$-$X4_{CET}$, $K_{PPT}$, $X1_{PPT}$-$X4_{PPT}$, $K_{CPT}$, $X1_{CPT}$-$X4_{CPT}$, $K_{AP}$, $X1_{AP}$-$X4_{AP}$, $K_{ON}$, $X1_{ON}$-$X3_{ON}$ are constants that were developed using linear regression analysis of hydrocarbon data from HPLC, and which are given in Table 4.

TABLE 4

| Constants | Cetane Number | Pour Point | Cloud Point | Aniline Point | Octane Number |
|---|---|---|---|---|---|
| K | 272.6 | 355.3 | 265.2 | 234.3 | 273.4 |
| X1 | −220.8 | −425.5 | −317.9 | −163.9 | −230.8 |
| X2 | −79.3 | −46.7 | −25.0 | −43.8 | 36.2 |
| X3 | 5.9 | 22.4 | 5.8 | −13.4 | −138.9 |
| X4 | −3.3 | 60.4 | 37.0 | −38.6 | — |

The following example is provided to demonstrate an application of equations (6) through (10). A sample of Arabian medium crude with a 15° C./4° C. density of 0.8828 Kg/l was analyzed by HPLC, using the described method. The HPLC composition was determined to be: Saturates=27.2 W %; 1-Ring Aromatics=18.6 W %; 2-Ring Aromatics 28.5 W %; and 3+-Ring Aromatics=25.7 W %.

Applying equation (6) and the constants from Table 4, $$\text{Cetane Number } (CET) = K_{CET} + X1_{CET} * DEN + X2_{CET} * SAT +$$
$$X3_{CET} * AROM - 1R + X4_{CET} * AROM - 2R$$
$$= (272.6) + (-220.8)(0.8828) + (-79.3)(0.272) +$$
$$(5.9)(0.186) + (-3.3)(0.285)$$
$$= 56.3$$

Applying equation (7) and the constants from Table 4, $$\text{Pour Point } (PPT) = K_{PPT} + X1_{PPT} * DEN + X2_{PPT} * SAT +$$
$$X3_{PPT} * AROM - 1R + X4_{PPT} * AROM - 2R$$
$$= (355.3) + (-425.5)(0.8828) + (-46.7)(0.272) +$$
$$(22.4)(0.186) + (60.4)(0.285)$$
$$= -12$$

Applying equation (8) and the constants from Table 4, $$\text{Cloud Point } (CPT) = K_{CPT} + X1_{CPT} * DEN + X2_{CPT} * SAT +$$
$$X3_{CPT} * AROM - 1R + X4_{CPT} * AROM - 2R$$
$$= (265.2) + (-317.9)(0.8828) + (-25.0)(0.272) +$$
$$(5.8)(0.186) + (37.0)(0.285)$$
$$= -11$$

Applying equation (9) and the constants from Table 4, $$\text{Aniline Point} (AP) = K_{AP} + X1_{AP} * DEN + X2_{AP} * SAT +$$
$$X3_{AP} * AROM - 1R + X4_{AP} * AROM - 2R$$
$$= (234.3) + (-163.9)(0.8828) + (-43.8)(0.272) +$$
$$(-13.4)(0.186) + (-38.6)(0.285)$$
$$= 64$$

Applying equation (10) and the constants from Table 4, $$\text{Octane Number } (ON) = K_{ON} + X1_{ON} * DEN + X2_{ON} *$$
$$SAT + X3_{ON} * AROM - 1R$$
$$= (273.4) + (-230.8)(0.8828) +$$
$$(36.2)(0.272) + (-138.9)(0.186)$$
$$= 54$$

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to *In re Beauregard*, 35 USPQ2d 1383 (U.S. Pat. No. 5,710,578), the present invention contemplates and includes this type of computer readable media within the scope of the invention. In certain embodiments, pursuant to *In re Nuijten*, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figure; however, modifications will be apparent to those of ordinary skill in the art and the scope of protection for the invention is to be defined by the claims that follow.

We claim:

1. A system for assigning an indicative property to a gas oil fraction or a naphtha fraction of an oil sample, based upon high pressure liquid chromatography (HPLC) data, wherein the oil sample is selected from the group consisting of crude oils, bitumens, heavy oils and shale oils, the system comprising:
    a non-volatile memory device that stores calculation modules and data, the data including HPLC data indicative of analyte retention time obtained from analysis of the oil sample;
    a processor coupled to the memory;
    a first calculation module that calculates the saturates and aromatic composition of the oil sample from the HPLC data, and that stores the saturates and aromatic composition into the non-volatile memory device; and
    a second calculation module that calculates and assigns the indicative property of the gas oil fraction or the naphtha fraction as a function of the saturates and aromatic composition of the oil sample and a density of the oil sample, and that stores the indicative property into the non-volatile memory device.

2. The system of claim 1, wherein the function in the second calculation module is a multi-variable equation with predetermined constant coefficients developed using linear regression techniques, wherein the variables are
the density of the oil sample,
the fraction of saturates as determined from the HPLC data of the oil sample, and
one or both of the
the fraction of aromatics containing 1-ring molecules as determined from the HPLC data of the oil sample, and the fraction of aromatics containing 2-ring molecules as determined from the HPLC data of the oil sample.

3. A system for assigning an indicative property to a gas oil fraction or a naphtha fraction of an oil sample, wherein the oil sample is selected from the group consisting of crude oils, bitumens, heavy oils and shale oils, the system comprising:
a high pressure liquid chromatography (HPLC) system that outputs HPLC data;
a non-volatile memory device that stores calculation modules and data, the data including outputted HPLC data indicative of analyte retention time obtained from analysis of the oil sample;
a processor coupled to the memory;
a first calculation module that calculates the saturates and aromatic composition of the oil sample from the HPLC data; and
a second calculation module that calculates and assigns the indicative property of the gas oil fraction or the naphtha fraction as a function of the saturates and aromatic composition of the oil sample and a density of the oil sample, and that stores the indicative property into the non-volatile memory device.

4. The system of claim 3, wherein the function in the second calculation module is a multi-variable equation with predetermined constant coefficients developed using linear regression techniques, wherein the variables are
the density of the oil sample,
the fraction of saturates as determined from the HPLC data of the oil sample, and
one or both of the
the fraction of aromatics containing 1-ring molecules as determined from the HPLC data of the oil sample, and the fraction of aromatics containing 2-ring molecules as determined from the HPLC data of the oil sample.

5. A method for assigning an indicative property to a gas oil fraction or a naphtha fraction of an oil sample based upon high pressure liquid chromatography (HPLC) data, wherein the oil sample is selected from the group consisting of crude oils, bitumens, heavy oils and shale oils, the method comprising:
entering into a non-volatile memory of a computer a density of the oil sample and HPLC data indicative of analyte retention time obtained from analysis of the oil sample;
calculating and assigning the saturates and aromatic composition of the oil sample from the HPLC data, and entering saturates and aromatic composition into the non-volatile memory of the computer; and
calculating and assigning the indicative property of the gas oil fraction or the naphtha fraction as a function of the saturates and aromatic composition of the oil sample and a density of the oil sample, and entering the indicative property into the non-volatile memory of the computer.

6. The method of claim 5, wherein the oil sample is crude oil.

7. The method of claim 5, wherein the oil sample is obtained from an oil well, stabilizer, extractor, or distillation tower.

8. The method of claim 5, wherein the indicative property is a cetane number.

9. The method of claim 5, wherein the indicative property is a pour point.

10. The method of claim 5, wherein the indicative property is a cloud point.

11. The method of claim 5, wherein the indicative property is an aniline point.

12. The method of claim 5, wherein the indicative property is an octane number.

13. The method of claim 5, wherein plural indicative properties are calculated including at least two indicative properties selected from the group consisting of cetane number, pour point, cloud point, aniline point and octane number.

14. The method of claim 5, wherein the oil sample is crude oil, and wherein the indicative property is assigned to the gas oil fraction of the oil sample and is selected from the group consisting of a cetane number, a pour point, a cloud point and an aniline point.

15. The method of claim 5, wherein the oil sample is crude oil, and wherein the indicative property is assigned to the naphtha fraction of the oil sample and an octane number.

16. The method of claim 5, wherein the function for calculating and assigning the indicative property is a multi-variable equation with predetermined constant coefficients developed using linear regression techniques, wherein the variables are
the density of the oil sample,
the fraction of saturates as determined from the HPLC data of the oil sample, and
one or both of the
the fraction of aromatics containing 1-ring molecules as determined from the HPLC data of the oil sample, and the fraction of aromatics containing 2-ring molecules as determined from the HPLC data of the oil sample.

17. The method of claim 5, wherein the function for calculating and assigning the indicative property is a multi-variable equation with predetermined constant coefficients developed using linear regression techniques, wherein the variables are
the density of the oil sample,
the fraction of saturates as determined from the HPLC data of the oil sample, and
one or both of the
the fraction of aromatics containing 1-ring molecules as determined from the HPLC data of the oil sample, and the fraction of aromatics containing 2-ring molecules as determined from the HPLC data of the oil sample.

18. A method for assigning an indicative property to a gas oil fraction or a naphtha fraction of an oil sample, wherein the oil sample is selected from the group consisting of crude oils, bitumens, heavy oils and shale oils the method comprising:
obtaining high pressure liquid chromatography (HPLC) data from a HPLC system, the HPLC data indicative of analyte retention time of the oil sample, obtaining a density of the oil sample;
entering into the computer the density of the oil sample and the HPLC data;
calculating and assigning the saturates and aromatic composition of the oil sample from the HPLC data, and entering saturates and aromatic composition into the non-volatile memory of the computer; and
calculating and assigning the indicative property of the gas oil fraction or the naphtha fraction as a function of the saturates and aromatic composition of the oil sample and a density of the oil sample, and entering the indicative property into the non-volatile memory of the computer.

19. The method of claim 18, wherein the oil sample is crude oil, and wherein the indicative property is assigned to the gas oil fraction of the oil sample and is selected from the group consisting of a cetane number, a pour point, a cloud point and an aniline point.

20. The method of claim 18, wherein the oil sample is crude oil, and wherein the indicative property is assigned to the naphtha fraction of the oil sample and an octane number.

\* \* \* \* \*